US011368000B2

(12) United States Patent
Guthrie et al.

(10) Patent No.: US 11,368,000 B2
(45) Date of Patent: Jun. 21, 2022

(54) ION GENERATOR DEVICE

(71) Applicant: NATURION PTE. LTD., Bukit Merah Central (SG)

(72) Inventors: Warren Edwin Guthrie, West Olive, MI (US); John Gregory Videtich, Zeeland, MI (US); Kenneth James Orr, Holland, MI (US); Eric Joshua Emens, Grand Haven, MI (US)

(73) Assignee: NATURION PTE. LTD., Bukit Merah Central (SG)

( * ) Notice: Subject to any disclaimer, the term of this patent is extended or adjusted under 35 U.S.C. 154(b) by 213 days.

(21) Appl. No.: 16/634,434

(22) PCT Filed: Jul. 13, 2018

(86) PCT No.: PCT/IB2018/055203
§ 371 (c)(1),
(2) Date: Jan. 27, 2020

(87) PCT Pub. No.: WO2019/021102
PCT Pub. Date: Jan. 31, 2019

(65) Prior Publication Data
US 2020/0169066 A1 May 28, 2020

Related U.S. Application Data

(60) Provisional application No. 62/537,664, filed on Jul. 27, 2017.

(51) Int. Cl.
*H01T 23/00* (2006.01)
*A61L 9/22* (2006.01)
(Continued)

(52) U.S. Cl.
CPC ............... *H01T 23/00* (2013.01); *A61L 9/22* (2013.01); *B03C 3/368* (2013.01); *B03C 3/38* (2013.01);
(Continued)

(58) Field of Classification Search
None
See application file for complete search history.

(56) References Cited

U.S. PATENT DOCUMENTS 7,408,562 B2   8/2008   Kotsuji
8,445,863 B2   5/2013   Nishida
(Continued)

FOREIGN PATENT DOCUMENTS

CN   2307944 Y   2/1999
CN   2569382 Y   8/2003
(Continued)

OTHER PUBLICATIONS

Dal Kyong Lee, International Search Report issued in related PCT /IB2018/055203, 3 pages, Republic of Korea.
(Continued)

*Primary Examiner* — Stephen W Jackson
(74) *Attorney, Agent, or Firm* — McGarry Bair PC (57) ABSTRACT

An ion generating device can include a housing having an opening, an anode and a cathode disposed within the housing and having a space between them in fluid communication with the opening, a power source having a negative terminal and a positive terminal with a first connection between the negative terminal and the anode and a second connection between the positive terminal and the cathode, and an air mover disposed to direct an air flow through the space and out of the opening.

17 Claims, 12 Drawing Sheets

(51) Int. Cl.
*B60H 3/00* (2006.01)
*F24F 8/192* (2021.01)
*B03C 3/36* (2006.01)
*B03C 3/38* (2006.01)
*B03C 3/41* (2006.01)
*B03C 3/60* (2006.01)
*F24F 3/16* (2021.01)
*F24F 8/30* (2021.01)

(52) U.S. Cl.
CPC ............... *B03C 3/41* (2013.01); *B03C 3/60* (2013.01); *B60H 3/0071* (2013.01); *F24F 3/16* (2013.01); *F24F 8/192* (2021.01); *A61L 2209/16* (2013.01); *B03C 2201/06* (2013.01); *F24F 8/30* (2021.01)

(56) References Cited

U.S. PATENT DOCUMENTS

| | | | |
|---|---|---|---|
| 8,559,157 B2 * | 10/2013 | Nishida | H01T 23/00 |
| | | | 361/230 |
| 8,691,158 B2 * | 4/2014 | Hanai | F24F 8/192 |
| | | | 422/306 |
| 8,771,599 B2 * | 7/2014 | Funabiki | A61L 9/22 |
| | | | 422/116 |
| 9,005,529 B2 * | 4/2015 | Tsuda | A61L 9/22 |
| | | | 422/120 |
| 9,330,889 B2 | 5/2016 | Denning et al. | |
| 9,588,161 B2 | 3/2017 | Savich | |
| 2006/0073085 A1 | 4/2006 | Chen et al. | |
| 2011/0015592 A1 | 6/2011 | Funabiki et al. | |
| 2012/0008592 A1 | 4/2012 | Nishida | |
| 2015/0004167 A1 | 2/2015 | Kaisha | |
| 2015/0041675 A1 | 2/2015 | Shibata et al. | |

FOREIGN PATENT DOCUMENTS

| | | | |
|---|---|---|---|
| CN | 1441207 | A | 9/2003 |
| CN | 1445894 | A | 10/2003 |
| CN | 1788181 | A | 6/2006 |
| CN | 1846337 | A | 10/2006 |
| CN | 101277724 | A | 10/2008 |
| CN | 101293169 | A | 10/2008 |
| CN | 101604822 | A | 12/2009 |
| CN | 201408913 | Y | 2/2010 |
| CN | 201805145 | U | 4/2011 |
| CN | 103250312 | A | 8/2013 |
| CN | 104220760 | A | 12/2014 |
| CN | 104284506 | A | 1/2015 |
| CN | 105337172 | A | 2/2016 |
| CN | 205549236 | U | 9/2016 |
| CN | 106229815 | A | 12/2016 |
| CN | 106486894 | A | 3/2017 |
| CN | 208422848 | U | 1/2019 |
| EP | 3193417 | A1 | 7/2017 |
| JP | 2005-243288 | A | 9/2005 |
| KR | 10-2012-001876 | A | 3/2012 |
| KR | 101119078 | B1 | 3/2012 |
| WO | 2010120072 | A2 | 10/2010 |

OTHER PUBLICATIONS

Chinese Patent Office, Office Action re Corresponding Application No. 201880049149.5, dated Mar. 16, 2021, 9 pages, China.
Chinese Patent Office, Office Action re Corresponding Application No. 201880049186.6, dated Mar. 2, 2021, 9 pages, China.
Li Chongli et al., "Chemical Plant Security Engineering", Aug. 31, 1986, 4 pages.
Chinese Patent Office, Office Action re Corresponding Application No. 201880049186.6, dated Mar. 16, 2022, 8 pages, China.

* cited by examiner

ION GENERATOR DEVICE

CROSS REFERENCE TO RELATED APPLICATION

This application is a National Phase application of International Application No. PCT/IB2018/055203, filed Jul. 13, 2018, which claims the benefit of U.S. Provisional Application Ser. No. 62/537,664 filed Jul. 27, 2017, both of which are incorporated herein by reference in its entirety.

BACKGROUND OF THE INVENTION

Negative air ion generation can be used as a means to clean air. The theory of operation is electrons are added to air molecules (i.e. "generating ions") by applying an electric field to spaced surfaces, generating negatively charged air particles passing between the spaced surfaces. These negatively charged particles bond to air-borne pollutants suspended in environmental or ambient air and subsequently move or are drawn to positively charged surfaces like walls and floors. The overall process moves pollutants from the air in a defined space to other places (e.g. walls and floors) that can be easily cleaned with traditional methods.

BRIEF DESCRIPTION OF THE INVENTION

In one aspect, the present disclosure relates to an ion generating device including a housing having an opening, an anode and a cathode disposed within the housing and having a space between them, a power source having a negative terminal and a positive terminal with a first connection between the negative terminal and the anode and a second connection between the positive terminal and the cathode, a fluid conduit defining an interior and fluidly connected with the opening, an air mover disposed to direct an air flow through the space into the fluid conduit interior and out of the opening, at least one needle disposed relative to the fluid conduit such that the at least one needle is exposed to the interior of the fluid conduit, the at least one needle conductively connected with the anode, and a conductive surface disposed in the interior of the fluid conduit and conductively connected to the cathode, the conductive surface spaced from the at least one needle.

DESCRIPTION OF EMBODIMENTS OF THE INVENTION

Aspects of the disclosure relate broadly to a device and method for injecting ions into a stream of air, in particular negative ions. The device, method, or process including aspects of the disclosure can consist of projecting a stream of electrons that are attached to air molecules, and thus, results in a current flow from the ion generator into the room. If any factor reduces the electron flow, then the device, method, or process has reduced effectiveness or fewer electrons or ions. Aspects of the disclosure can include methods or apparatus to overcome factors that reduce current flow in air ion generators. In another aspect, the disclosure relates to a device and method for injecting ions into a stream of air for providing a stable production of ions, and can improve the flow of ions (electrons) into a desired space or environment.

As used herein, a "defined space" refers to a region that contains the ion generator and is separated from a larger space by a partition. For example, a bedroom, hospital room, or vehicle interior. While "a set of" various elements will be described, it will be understood that "a set" can include any number of the respective elements, including only one element. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to each other. In non-limiting examples, connections or disconnections can be selectively configured to provide, enable, disable, or the like, an electrical connection between respective elements. The exemplary drawings are for purposes of illustration only and the dimensions, positions, order and relative sizes reflected in the drawings attached hereto can vary.

Generally, at least two factors can reduce ion generation current flow into the room. The first factor can include that the negative ion generation process can cause surfaces of the ion generator to become negatively charged and, as such, will tend to repel like-charged particles, including negative air ions. The term for this phenomena is "charge build-up." The result is lower electron flow the longer the ion generator operates.

The second factor can include that current must flow through a closed path. In the case of an air ion generator, such as aspects disclosed herein, the closed path can includes the air in the space around the generator or between the spaced conductive surfaces, such as an anode element and a cathode element. As such, the range that ions are projected will naturally only include the current return path.

If the return path does not include surfaces surrounding the defined space, then, even though ions might be produced, they are not projected into the intended space. The term for this phenomenon is "ion confinement."

Aspects of the disclosure can include reducing the effects of charge build-up on surfaces of the ion generator, especially those nearby the ion source by treating at least one surface with conductive material. The surface treated with conductive material can provide an electrical path to remove the negative charge so that negative charge does not collect on the surface and subsequently repel the ions. The conductive material can include an electrically conductive path to, for example, the positive terminal (also referred to as the "cathode") of the associated electron current source.

In one example aspect of the disclosure, to reduce the effects of ion confinement, the electron's source return path can be electrically coupled to an electrical ground, including, in one non-limiting example, building wiring. For example, using building wiring for a ground connection for the uses of air ionizers, can be utilized wherein no direct Earth grounding is provided, or wherein the user is unlikely to adapt the building to use the product. In aspects of the disclosure, the current path can be provided with a connection of the electron source to building wiring. The connection is most effective when the means includes the building's Earth ground (for instance, the 'green wire') because many common features in buildings are connected to Earth such as conduits, water pipes, floors, foundations etc. However, in many instances, Earth ground is not available to the ion generator. In this case, an alternative or additional means is to provide a connection through a resistive path to building wiring. The connection to the building wiring provides a convenient and effective method of providing a path that is less directly connected to building features, but nonetheless highly effective compared to providing no current return path. Connection to building wiring usually provides a sufficient yet ad-hoc return path for current and is appropriate for situations where the cost of adding an intentional return path is not warranted.

To reduce the effects of ion confinement, there is another configuration for embodiments of the disclosure, which provides a current path by adding, applying, or layering at least one conductive surface to the defined space which can be further electrically connected to the electron source. This method is appropriate in situations where the cost is justifiable such as an industrial or medical application. For example, a hospital room might include a conductive floor or a livestock barn might include a conductive screen on one or more walls.

Figure 1:
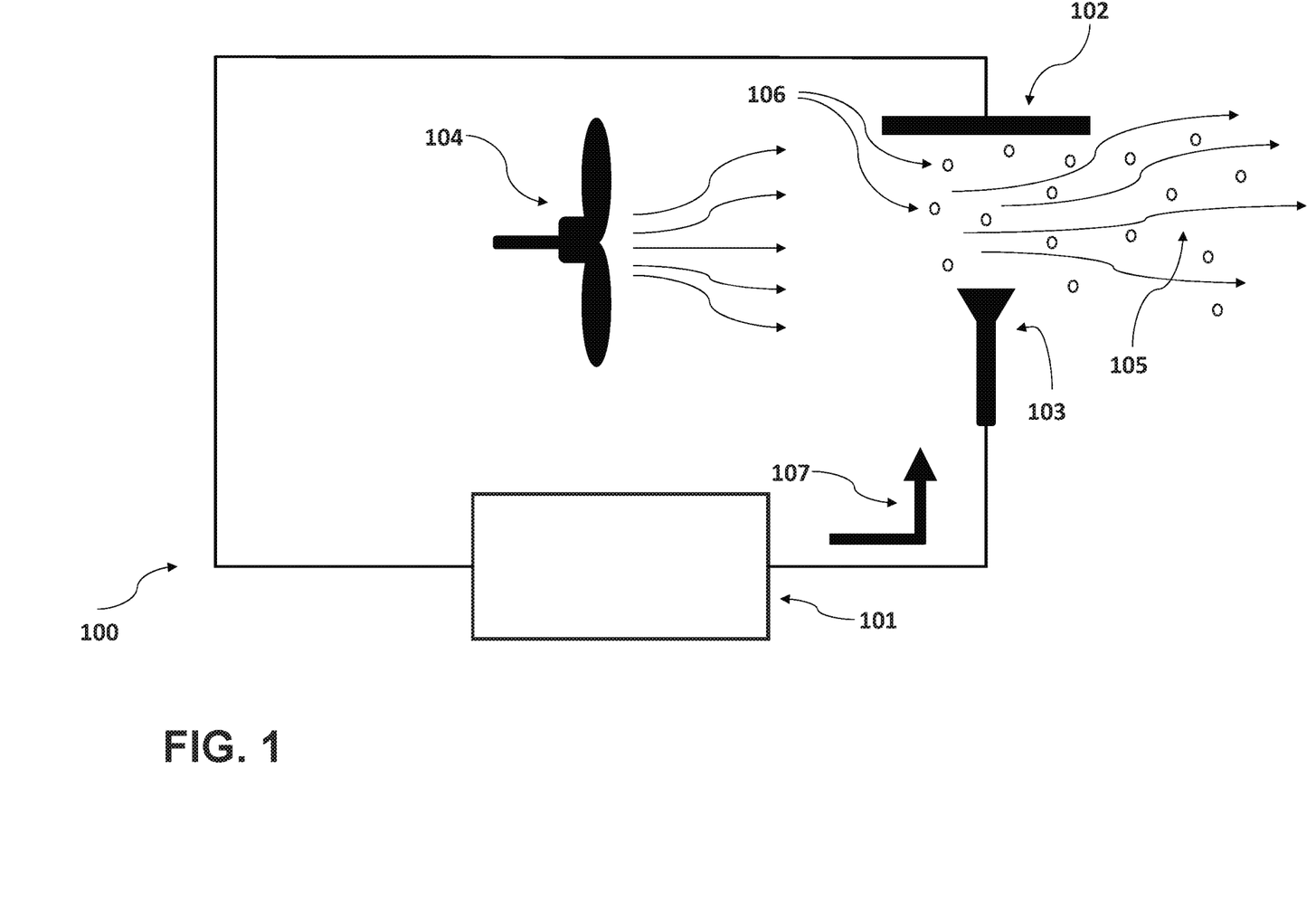
FIG. 1 shows a schematic drawing of a device for injecting ions into a stream of air, in accordance with various aspects described herein.

FIG. 1 shows an ion generating device 100 for injecting ions into a stream of air 105. The device uses a power source 101, such as a high voltage generator or source connected to a cathode 102 and anode 103. Electrons 107 flow (illustrated as an arrow) from the power source 101. Negative ions 106 are produced or generated in the region between the anode 103 and cathode 102. A fan 104 can blow or direct the ions 106 contained in a stream of air 105 or along a flow path 105.

Figure 2:
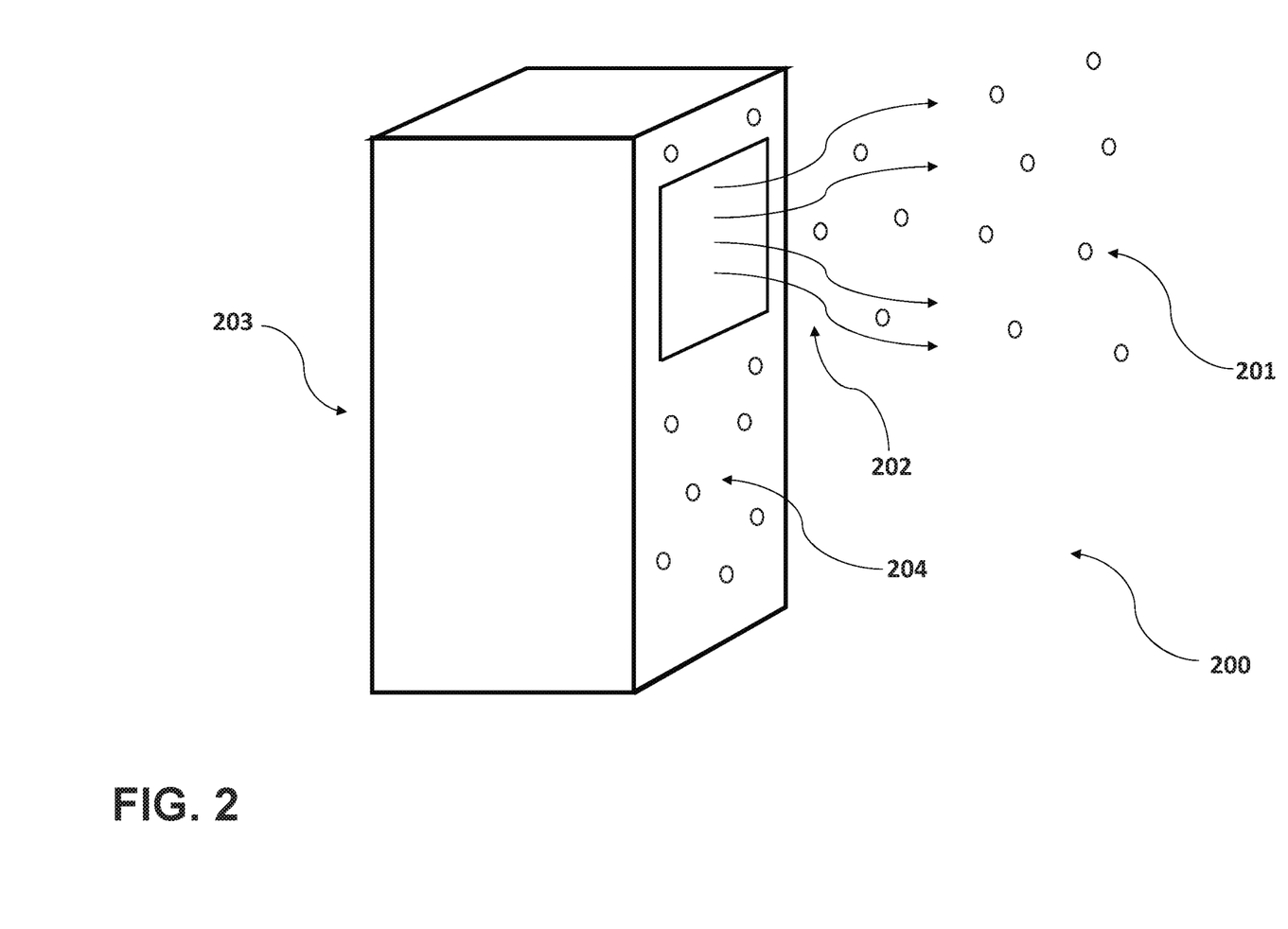
FIG. 2 shows an outer view of a device for injecting ions into a stream of air, emphasizing charge build-up, in accordance with various aspects described herein.

FIG. 2 shows a perspective view of an ion generating device 200 having a housing 203, according to another aspect. The ion generating device 200 operates similar to the device 100 illustrated in FIG. 1, by injecting ions 201 into a stream of air 202. The device includes the housing 203, illustrating a charge build-up 204 on the surface.

Figure 3:
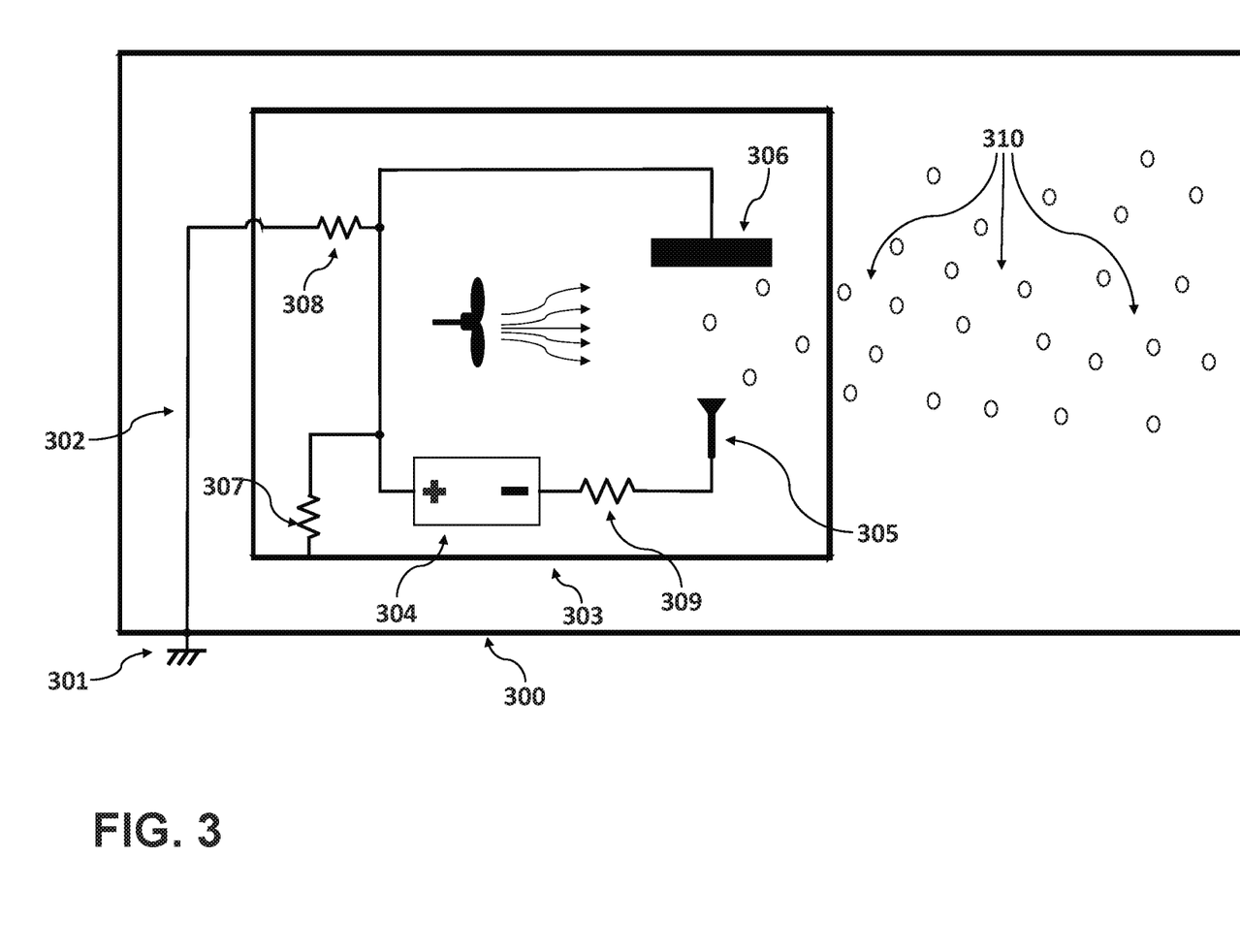
FIG. 3 shows a schematic circuit diagram of the electric circuits in accordance with various aspects described herein.

FIG. 3 shows a schematic diagram that includes an ion generating device according to aspects of the disclosure for improving ion consistency. A defined space 300, such as a room, a car, or an enclosed volume, can include at least one electrical connection to an electrical ground 301, which can include in one non-limiting example Earth ground. The electrical ground 301 connection is further electrically connected by wire 302 to the ion generator 303 through resistor 307, which connects to at least one surface of the ion generator 303. The surfaces of the ion generator 303 can include a cathode 306 and a spaced anode 305. The cathode 306 is also connected though a resistor 308 to ground 301. A power source 304, such as a high voltage generator, is connected through a current-limiting resistive element 309, such as a protection resistor, to the anode 305. The current-limiting resistive element 309 can be selected to provide protection for inadvertent human contact to the anode. The coupling of the power source 304 to the cathode 306 and anode 305 creates an electric field between the cathode 306 and anode 305. The electric field, in turn, generates or produces a set of negative ions 310 in the ambient air occupying or traversing the electric field. The negative ions 310 proceed into the ambient space 300 because they are attracted to the higher voltage potential of the materials defining the space, such as the wall or floor, as previously described. As shown, the materials defining the space can have a higher voltage potential because they are connected to the electrical ground 301.

Figure 4:
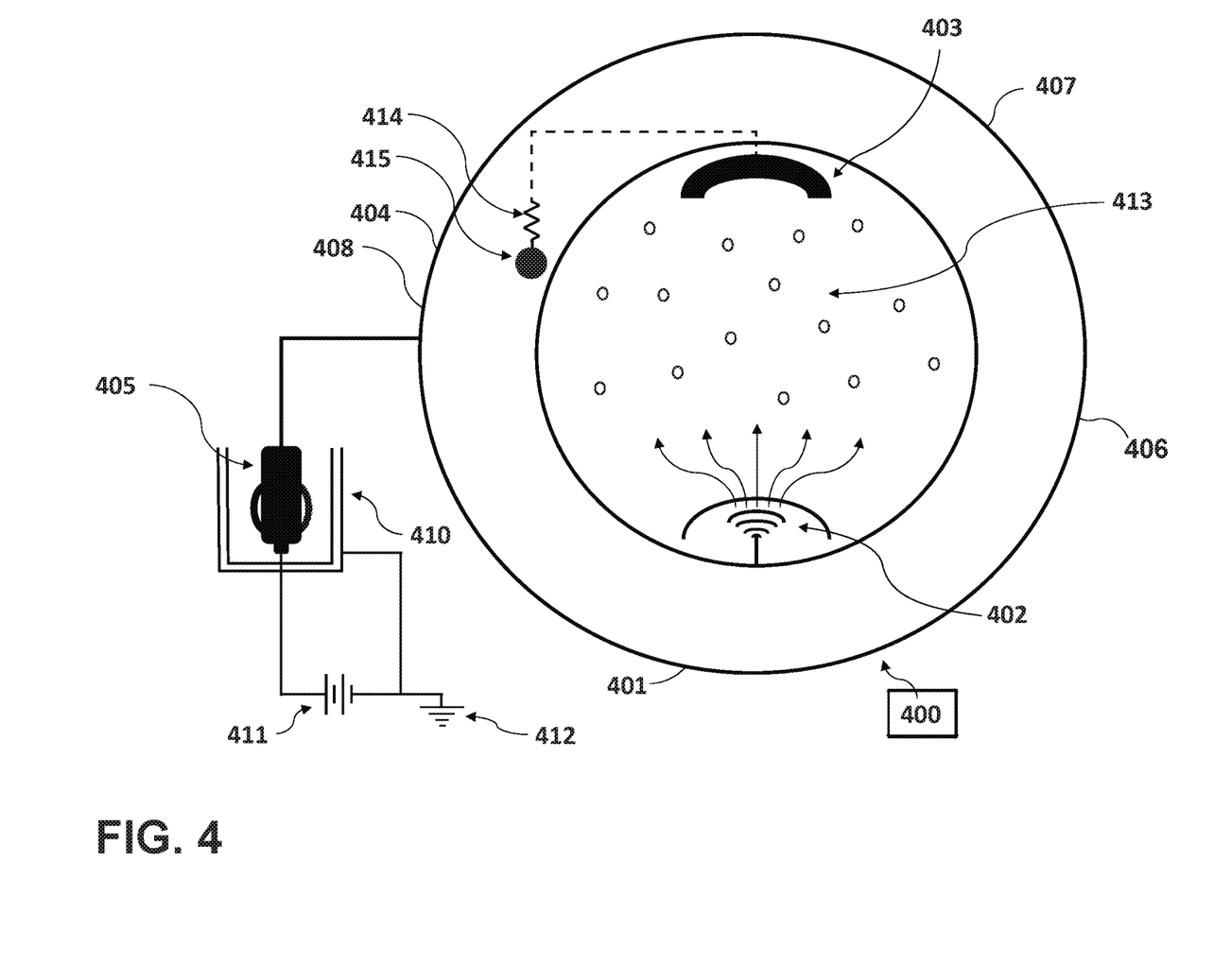
FIG. 4 shows a circuit diagram for use in a vehicle, in accordance with various aspects described herein.

FIG. 4 diagrams another aspect of the disclosure configured for use as an ion generating device 400 for application to a vehicle, such as an automobile. While an automobile is described, embodiments of the disclosure can be equally applicable in aircraft or aqueous-based vehicles, wherein a volume of ambient air can be occupied with negative ions. As previously described, a power source 406, such as a high voltage generator is connected to cathode 403 and anode 402 through a protection resistor 401. Ions 413 are produced in the region between cathode 403 and anode 402. A power connection 405 is provided through a power socket 410 to energize the power source 406, which for example can supply power from a battery 411 located in the vehicle. As such, the vehicle ground 412 is connected to the device through internal circuitry 408 and a connection 404 to the cathode 403. A conductive surface 407 is provided to mitigate charge buildup by connection 415 through resistor 414.

Figure 5:
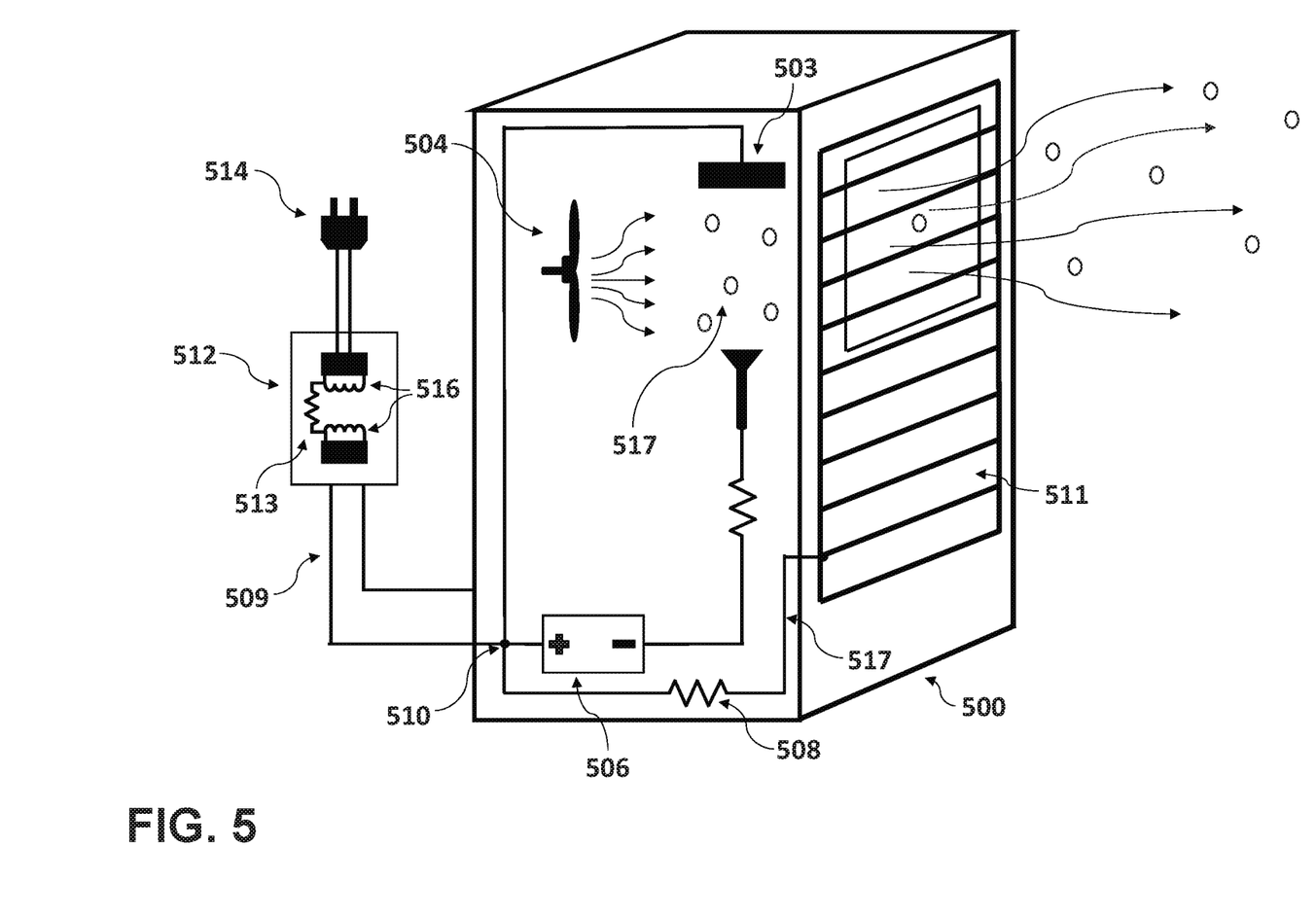
FIG. 5 shows a circuit diagram for use with an external transformer-isolated power supply, in accordance with various aspects described herein.

FIG. 5 shows an ion producing device 500 according to yet another aspect of the disclosure, including air stream 504 and ions 517. The ion generating device 500 can use an external power supply 512. In many cases, external power supplies provide ground isolation through a transformer 516. As such, a bridging resistor 513 provides a high resistance path that will still allow sufficient current flow as a counter measure to ion confinement. The diagram shows a connection 510 from the positive terminal of the power supply 506, such as a high voltage supply through the power supply leads 509 through the bridge resistor 513 to building wiring connection 514. Additionally, a connection 510 is provided to at least one selected outer surface 511 or to at least one inner surface 517 is provided by resistor 508. The ion producing device 500 can further include a cathode 503, as shown.

Figure 6:
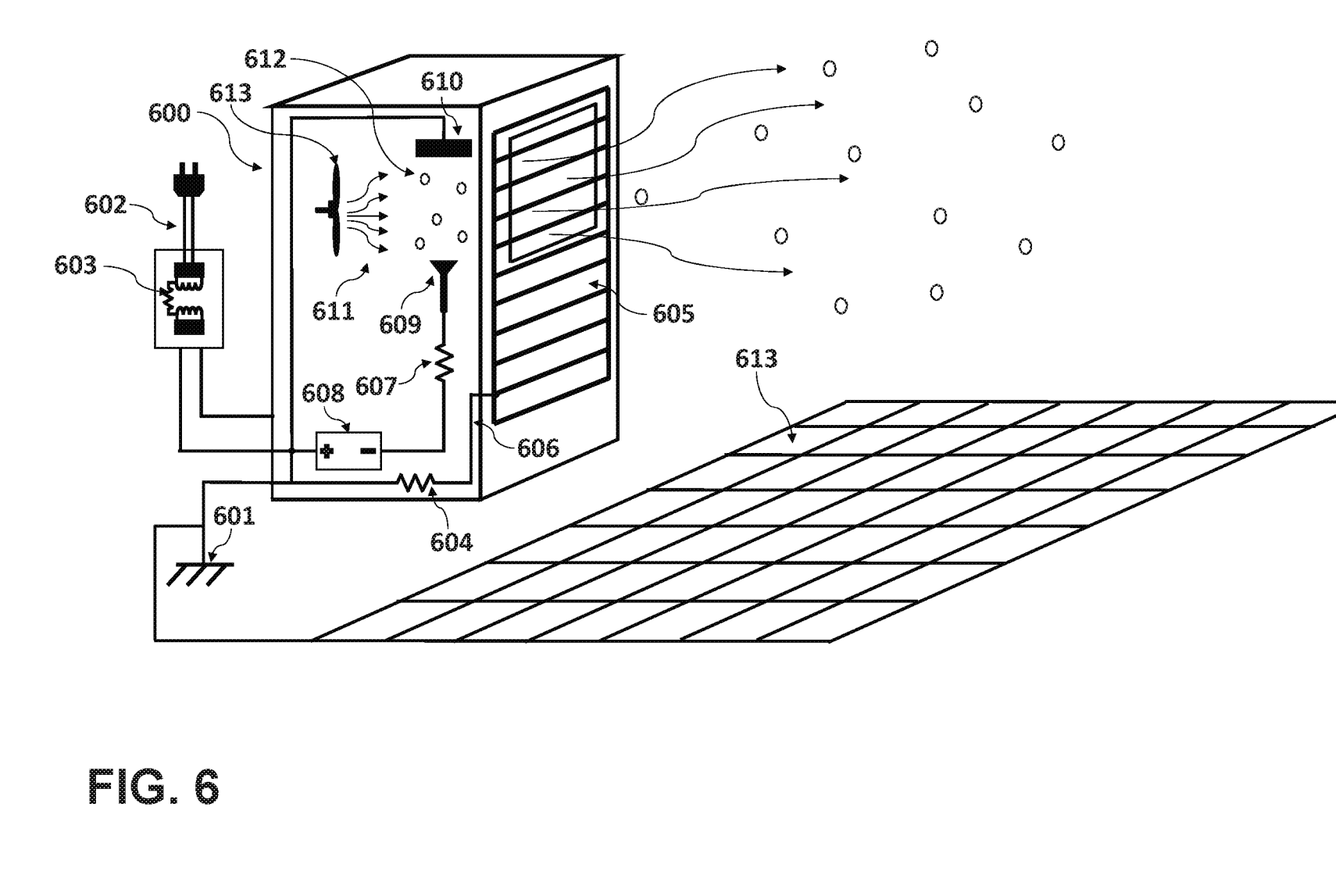
FIG. 6 shows a circuit diagram for use with an internal power supply, in accordance with various aspects described herein.

FIG. 6 shows yet another aspect of the disclosure having an ion producing device 600, producing ions 612 in a region between cathode 610 and anode 609. The anode 609 is connected to power supply 608, such as a high voltage power supply through a safety resistor 607. A fan 613 produces an air stream 611 to propel ions 612 from the volume between the spaced cathode 610 and anode 609 to the ambient space outside of the device 600. The device 600 can be configured to use a power supply 603, 608 electrically supported by, for example, mains power 602, such as a wall outlet. The power supply 602, 603, 608 can be internal or external to the device 600. In this example, electrical ground 601 is connected to the positive terminal of the power supply 608. The electrical ground 601 is also connect to at least one selected outer surface 605 or at least one selected inner surface 606 of the device 600. Optionally, a grounded grid or plate 613 is included to provide an external ion path as might be used in livestock barns or hospital rooms.

As previously described, charge buildup can result in ions being repelled from production to the exit point. By selectively coating the surfaces in the ion path, including but not limited to the inner surface 517, 606 or outer surface 511, 605, and connecting these to the cathode 102, 306, 403, 503, 610 the effects of charge buildup can be mitigated.

FIG. 3 diagrams schematically the connection of a surface of the ion generator 303 to the Cathode 306 through a resistor 308.

In one non-limiting aspect of the disclosure for a vehicle application, as in FIG. 4, a straightforward connection 415 of the conductive surface 407 through the resistor 414 to the cathode 403.

In one non-limiting aspect of the disclosure for a tabletop, floor-model, or commercial models, a similar conductive path is provided as diagrammed in FIGS. 5 and 6. The table/floor type connects conductive surface 511 through resistor 508 to connection 510 to Cathode 503.

The commercial application illustrated in FIG. 6 can be similar to the above-described aspects. The conductive surface 605 uses connection 606 through resistor 604 to connect with the cathode 610.

In aspects of the disclosure described herein, one or more separate resistors can be omitted since the conductive surface itself could be resistive.

Ion confinement can also be mitigated by providing a path for current to flow back to the respective cathode 102, 306, 403, 503, 610 after flowing through the space to be treated with ions. The path can include existing conductive or semi-conductive materials like water pipes, floors, or the like. In this aspect, the connection can exist between the system cathode 102, 306, 403, 503, 610 to those conductive materials. In FIG. 3, the cathode 306 connection is shown schematically as resistor 308 connected to Earth ground 301.

In the case of application to a vehicle, such as in the aspects of FIG. 4, the electrical ground is replaced by vehicle ground 412. As further shown in FIG. 4, the cathode 403 is connected by a series of connections 404, through internal circuitry 408, a power connection 405, through the power socket 410, to vehicle ground 412. Aspects of the disclosure can include a subset of the aforementioned connections, or additional connections.

In case of a table model or floor model, as shown in FIG. 5 the cathode 503 can be connected by way of connection 510 through power lead 509 to power supply 512, where the isolation transformer 516 includes a resistor 513, to allow connection to building wiring 514. In the case where an electrical ground connection is included (for example, with a grounded power connection), a direct connection can be made instead of a resistor across the isolation transformer. Aspects of the disclosure can include a subset of the aforementioned connections, or additional connections.

The direct connection can also be included in the embodiments of commercial applications, for example, as shown in FIG. 6. In FIG. 6, the cathode 610 is connected directly to electrical ground 601. In cases where are larger area is to be treated with ions, or where the building does not inherently include grounded features, and additional plate or screen 613 can be provided. This could be, for example, a wire mesh in the ceiling above a livestock barn or, a conductive floor in a hospital room.

Figure 7:
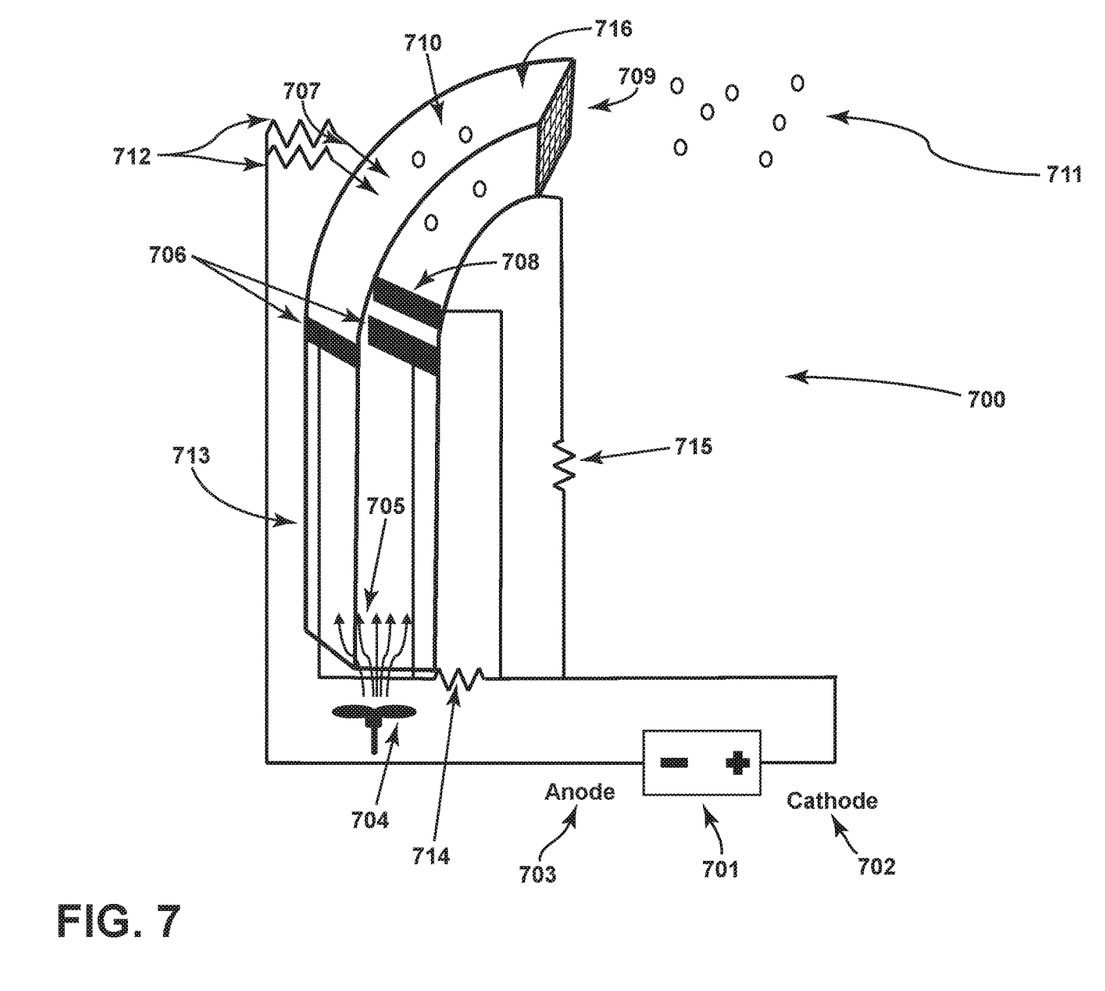
FIG. 7 shows a schematic drawing of another non-limiting device for injecting ions into a stream of air, in accordance with various aspects described herein.

FIG. 7 shows another non-limiting device 700 for injection ions 710 into the air 711 according to another non-limiting aspect of the present disclosure. The device 700 is similar to the earlier-described devices 100, 200, 300, 400, 500, 600; therefore, like parts will be identified with like numerals identified by the 700 series of numbers, with it being understood that the description of the like parts of the devices 100, 200, 300, 400, 500, 600 applies to the device 700, unless otherwise noted. As illustrated, a high voltage generator 701 has a cathode 702 and an anode 703. A fan 704 can be utilized to force air (schematically show as arrows 705) through a fluid conduit, including but not limited to, a duct 713 or ducting.

Non-limiting aspects of the duct 713 can include at least one internally-facing or internally-surfaced conductive surface 706 exposed to the air 705 and conductively connected to the cathode 702 through a resistance 714. Non-limiting aspects of the duct 713 can also include at least one externally-facing externally-surfaced conductive surface 708 on the outside of the duct 713, also conductively connected to the cathode 702. Yet another non-limiting aspect of the duct 713 can include a conductive screen 709 disposed, located, arranged, or the like, on or at the device air outlet 716 (i.e. where the air 205, 711 or ions 710 are exhausted or expelled from the device 700). The conductive screen 709 can be conductively connected to the cathode 702 through a resistor 715. Yet another non-limiting aspect of the duct 713 can include a set of sharp points, including but not limited to needles 707, positioned, arranged, disposed, or the like, such that the needles 707 or needle tips are exposed to the air 205, 711 or ions 710 traversing the duct 713. The set of needles 707 can be conductively connected to the anode 703 through a corresponding set of resistors 712. In this sense, the set of needles 707 can effectively operate as the ionizing anode of the device 700.

As described herein, charge buildup can result in ions being repelled from the exit point, thereby not reaching the intended destination, external to the device 700. In FIG. 7, these built up charges are readily dissipated by providing an electrical connection from the cathode 202 to the potential repelling surfaces 706, 708. However, this connection has the potential to dissipate a significant number of these ions if the respective resistance of the connecting resistor 714 is too low. One aspect of the disclosure can include selecting a resistor 714 or set of resistors 714, 715, 712 to selectively maintain a balance between allowing or enabling the charge to build up so high that it can at least partially repel ions while dissipating the built up ions by way of the conductive connection with the cathode 702.

In one non-limiting aspect, the balance can be maintained by properly selecting the resistor 714 or set of resistors 714, 715, 712 that connect the charged surfaces 706, 708 to the high voltage cathode 702. The value of resistor 714 or set of resistors 714, 715, 712 can further depends on location of the surfaces 706, 708 relative to the ion stream (e.g. where the surfaces 706, 708 are disposed relative to the duct 713, or a quantity or surface area of the surfaces 706, 708 exposed. Generally, a desired higher ion content requires a higher resistance value. For instance, too small of a screen 709 resistor 715 resistance (for example, less than 2.5 Gigaohms) can result in "short circuiting" the ions 710 prior to exiting the device 700 or duct 713. In another instance, too high of a screen 709 resistor 715 resistance (for example, greater than 15 Gigaohms) can repel ions 710 from the screen 709, reducing or interrupting the ionic air flow 711 exiting the device 700 or duct 713. In one non-limiting example value, a screen 709 resistor 715 resistance can be approximately 10 Gigaohms, which provides a balance between the too small and too high considerations described above.

Figure 8:
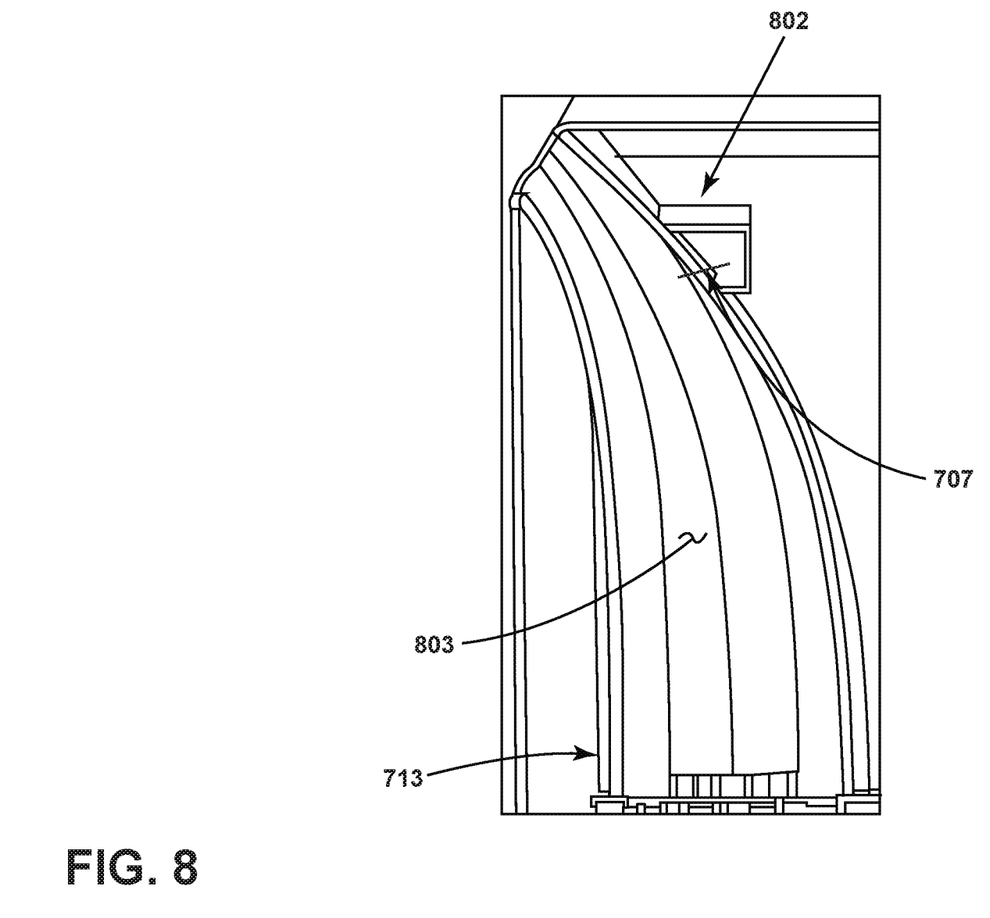
FIG. 8 shows a cross section of a duct and needle mount of the device of FIG. 7, in accordance with various aspects described herein.

FIG. 8 shows a cross-sectional view of a duct 713 of FIG. 7. As shown, a mounting 802 can be connected, attached, disposed, supported, or the like, wherein the mounting 802 includes the set of needles 707. At least one of the duct 713, the mounting 802, or the set of needles 707 can be selected or mounted in combination thereof, to enable, allow, or provide for the set of needles 707 (or for example, a distal end or tip of the needles 707), to be exposed to an internal cavity 803 defined by the duct 713, wherein the air or ions traverse during device operations.

Aspects of the disclosure can be included wherein the needle 707 material can affect the magnitude of produced ions. In one non-limiting aspect of the disclosure, the set of needles 707 can be selected based on a set of criteria including, but not limited to, durability, corrosion resistance, ability to be sharpened, conductivity to produces high ion current (e.g. because of the material atomic structure), or the like. One non-limiting aspect of this disclosure can utilize a set of tungsten needles 707. Tungsten is merely one non-limiting example of needle 707 construction. Additional needle 707 compositions can include, but are not limited to, sterling silver, gold-plated materials, rhodium plated materials, NiCr$_3$ welding rods, NiCr$_3$ welding rods with gold plating, or sewing needles.

In another aspect of the disclosure, needle 707 geometry, including but not limited to sharpness and diameter, can also affect ion current. Generally, a sharper needle 707 can produce more ion current. Below, is a comparison of ion current using a tungsten needle of 0.762 millimeter diameter, and various needle 707 tip configurations.

| Sharpness | Example Ion current |
| --- | --- |
| Flat tip (blunt) | 0 uA |
| Round tip (same diameter as needle) | 0.10 uA |
| 6 uM (estimated) tip | 0.44 uA |
| 3 uM tip | 0.48 uA |

Figure 9:
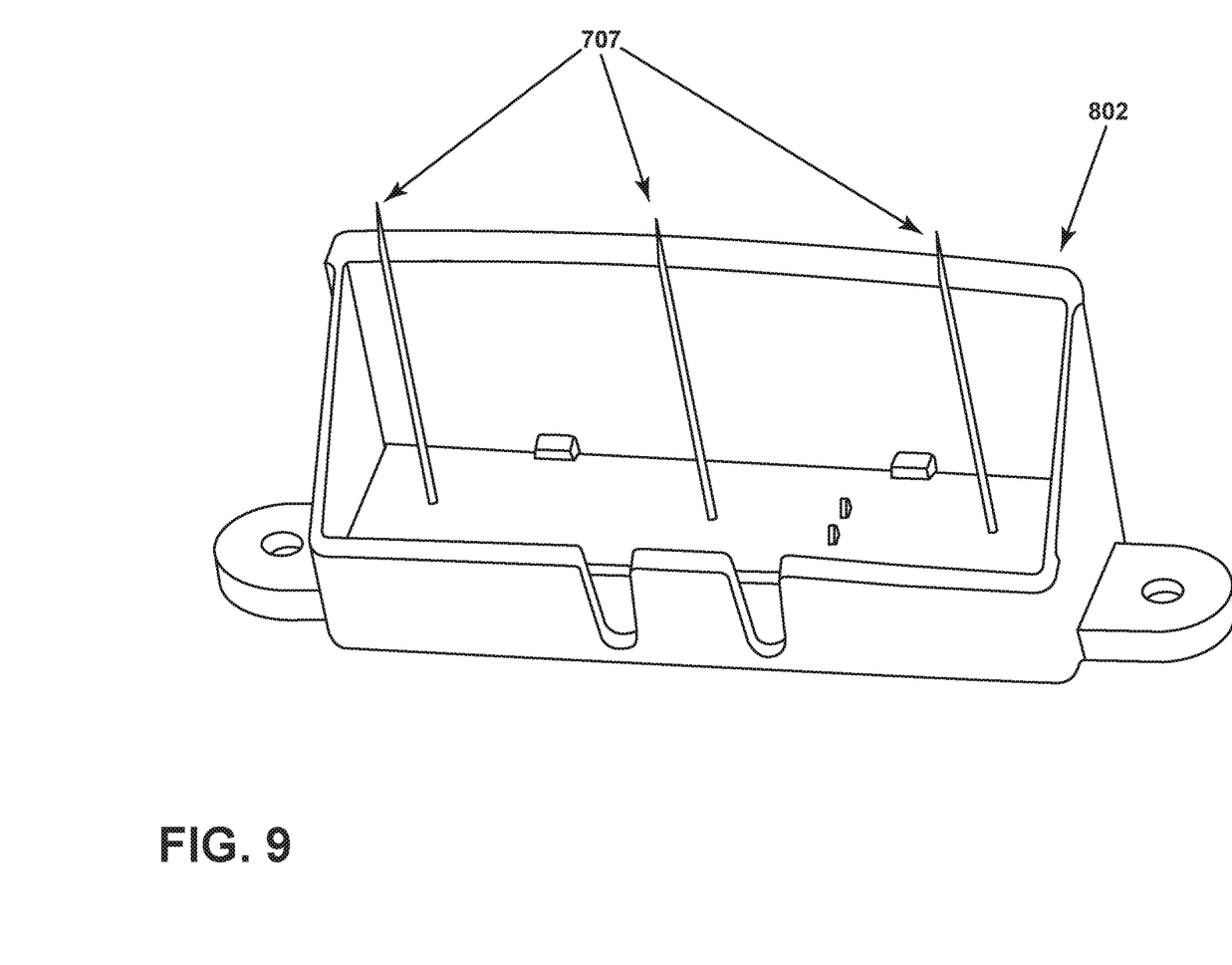
FIG. 9 shows an isometric view of the needle mount of FIG. 8, in accordance with various aspects described herein.

FIG. 9 illustrates a perspective view of one non-limiting example of the mounting 802 and set of needles 707, for example, having a tungsten needle tip sharpness less than 3 micrometers.

Figure 10:
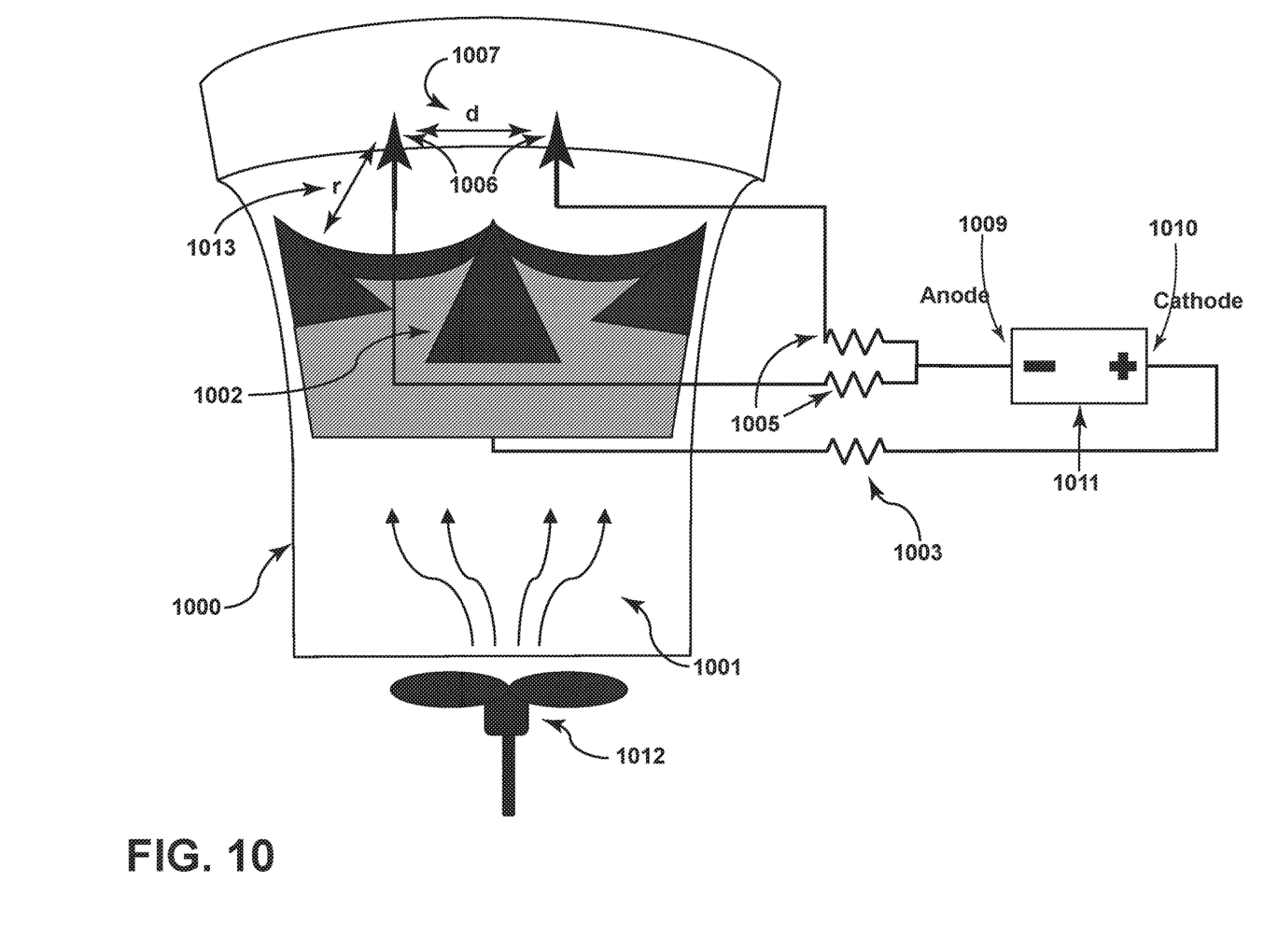
FIG. 10 shows a circuit diagram of the needle spacing from conductive surfaces of the device of FIG. 7, in accordance with various aspects described herein.

FIG. 10 illustrates electrical connections and geometry on the inside of an ion generator duct 1000 in accordance with another non-limiting aspect of the present disclosure. As shown, a high voltage generator 1011 has an anode 1009 and a cathode 1010. A set of needles, shown as two needles 1006 are connected to the anode 1009 through a resistors 1005, which can be similar to resistor 712, previously described. A conductive surface 1002 can be located on the interior of the duct 1000 and can be further conductively connected to cathode 1010 through a resistor 1003, which can be similar to resistor 714, previously described.

Non-limiting aspects of the disclosure can be included wherein the set of needles are separated by distance (d) 1007. Additional non-limiting aspects of the disclosure can be included wherein at least one of, or each of, the needles 1004 (e.g. the needle, or the needle tip or point) are spaced from the closest conductive surface 1002 by at least a constant distance forming a radius (r) 1013. As shown, each of the two illustrated needles 1006 has a radial spacing from a correspondingly arc-shaped conductive surface 1002. In this sense, the arc-shaping of the conductive surface 1002 relative to the set of needles 1006 ensures a constant or consistence radius (r) 1013 or radial range between the conductive surface 1002 and the set of needles 1006.

Air can be forced by a fan 1012 through the duct 1000, the air flow represented by arrows 1001. As shown, the set of needles 1006 can be located or positioned downstream of the conductive surface 1002 such that the air flow 1001 can first pass by the conductive surface 1002, followed by passing the set of needles 1006. The air flow 1001 can further exit the duct 1000 after passing the set of needles 1006.

High output ion generators can use or utilize high voltage which may potentially cause air dielectric breakdown and subsequent ozone. This breakdown will occur in the region between the needles 1006 and the charge removal metallization (i.e. the conductive surface 1002). Similar to the charge buildup/ion discharge balance discussed above, there is a balance between the effectiveness of the charge dissipation and allowed potential voltage (magnitude of the anode 1009 to cathode 1010 voltage). In one non-limiting example, this balance can be maintained by appropriately shaping and spacing the conductive surface 1002 used to dissipate the charge build up, in accordance with a set of considerations or criteria. In another non-limiting example, the shaping and spacing of the conductive surface 1002 can be relative to the set of needles 1006 or needle tips. In a first non-limiting consideration, the conductive surface 1002 dissipates built-up charges most effectively when it is proximate or close to the set of needles 1006. In another non-limiting consideration, the highest potential voltage is supported by the greatest separation, distance, or radius (r) 1013 between the set of needles 1006 and the conductive surface 1002. In a non-limiting example, when using 10,000 Volts potential it has been discovered that no air dielectric breakdown will occur and output ion generation will be optimized when distance (d) 1007 is approximately 100 millimeters and radius (r) 1013 is approximately 50 millimeters. The two-arc pattern is suited to correspond with the two ionization needles 1006, but could be replicated further if additional needles 1006 are included. The constant radius (r) 1013, arranged as an arc between the set of needles 1006 and the conductive surface 1002, can be one exemplary aspect wherein no single point on the conductive surface 1002 is closer to the set of needles 1006 or needle tip than any other single point. In one example, the arcing shape of the conductive surface 1002 can be referred to as a "crown" shape.

In one non-limiting aspect of the disclosure, the resistor 1003 can be selected based on, for instance, desired ion flow characteristics. For example, selecting a resistor 1003 having too low of a resistance (e.g. less than 0.2 Gigaohms) too low can result in "short circuiting" the ions to the conductive surface 1002 prior to the ions or air flow 1001 exiting the device or duct 1000. In another instance, a resistor 1003 having too high of a resistance (for example, greater than 2 Gigaohms) can repel ions from the conductive surface 1002, reducing or interrupting the ionic air flow 1001 exiting the device or duct 1000. In one non-limiting example value, a resistor 1003 resistance can be approximately 1 Gigaohms, which provides a balance between the too small and too high considerations described above.

In yet another aspect of the disclosure, the device can include a duct or duct system configured, arranged, or the like, to establish a "direct" or "unimpeded" air flow through the device. Some air purification methods do not depend on rapid transport of air from purifier to destination. However, ion-based purification, such as that described herein, is different. Ions have a limited "life" or effective "window" of purification functionality, as the ions will dissipate, or otherwise be removed from the ionized air flow by way of discharging through another charged particle or surfaces in the exhausted space.

As such, establishing a rapid path from ion generation to the intended destination will improve the effectiveness of ion air purification. In this sense, a "direct" or "unimpeded" air flow through the device will be one wherein the ions can directly move to the exhaust port or output without, or with less, unnecessary motion not parallel with the duct or ducting system path. In on non-limiting example, "cyclonic" movement is unnecessary motion as the circular motion has a component not parallel with the duct or ducting system path.

In one non-limiting example, more or faster exhaust air flow can be created by simply increasing the air speed, such as by increasing the fan speed). However, increased fan speed can cause additional noise and requires a more powerful and costly fan.

Figure 11:
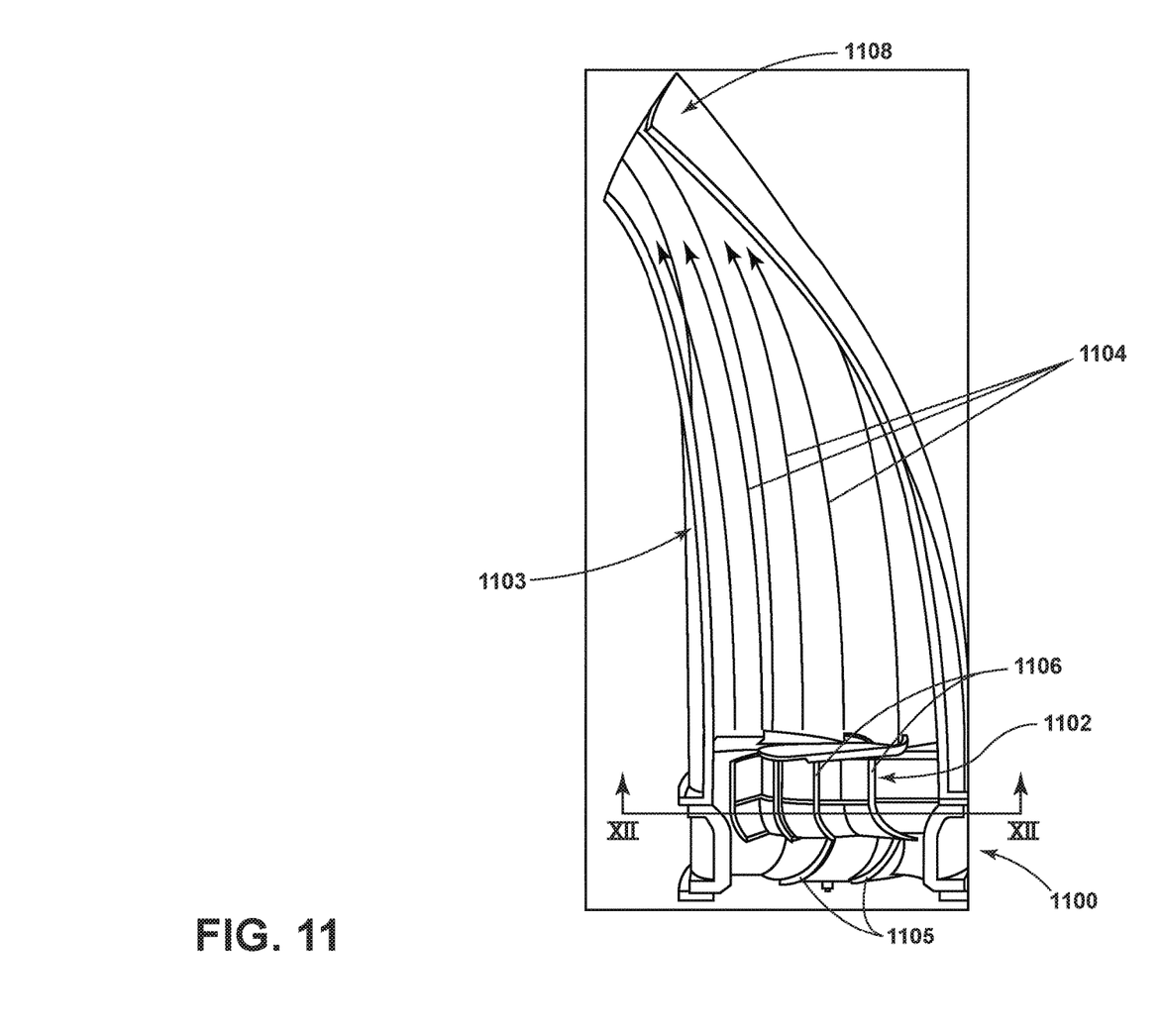
FIG. 11 shows a cross-sectional view of a duct for the device of FIG. 7 having a laminar flow device, in accordance with various aspects described herein.

One non-limiting aspect of the disclosure can allow for or provide a direct or unimpeded air flow (e.g. without, or with less cyclonic air flow, compared with conventional systems). FIG. 11 illustrates a cross-sectional view of a device 1100 having a duct 1103, a fan 1101, and a laminar flow device 1102. As shown, the fan 1101 can include fan blades 1105 that are angled or offset relative to the direction of air flow (schematically illustrated as arrows 1104). The laminar flow device 1102 can include stationary elements or laminar flow blades 1106 that are angled or offset in an opposite direction relative to the fan blades 1105.

During fan 1101 operation, the rotational movement of the fan blades 1105 forces air flow through the duct 1103. The rotational movement and the angling of the fan blades 1105 can cause, create, or the like, a naturally-occurring cyclonic motion on the resulting forced air flow. However, the naturally-occurring cyclonic motion of the resulting forced air flow is at least partially negated, removed, neutralized, or the like, when the air is forced through the laminar flow device 1102 and laminar flow blades 1106. Effectively, the inclusion of the laminar flow device 1102 allows the forced air flow 1104 to flow in parallel (as shown) through the duct 1103 with less non-parallel motion, relative to the duct 1103. Stated another way, the air flow 1104 currents are changed from cyclonic to laminar. Hence, they reach the intended destination downstream more quickly.

In one example configuration, the destination can include a tapered outlet portion 1108 of the duct 1103, wherein the tapered outlet portion 1108 is spaced from the fan 1101 or laminar flow device 1102. In this sense, air can be drawn in from an inlet proximate to the fan 1101, and be forced toward the tapered outlet portion 1108, downstream from the laminar flow device 1102.

Figure 12:
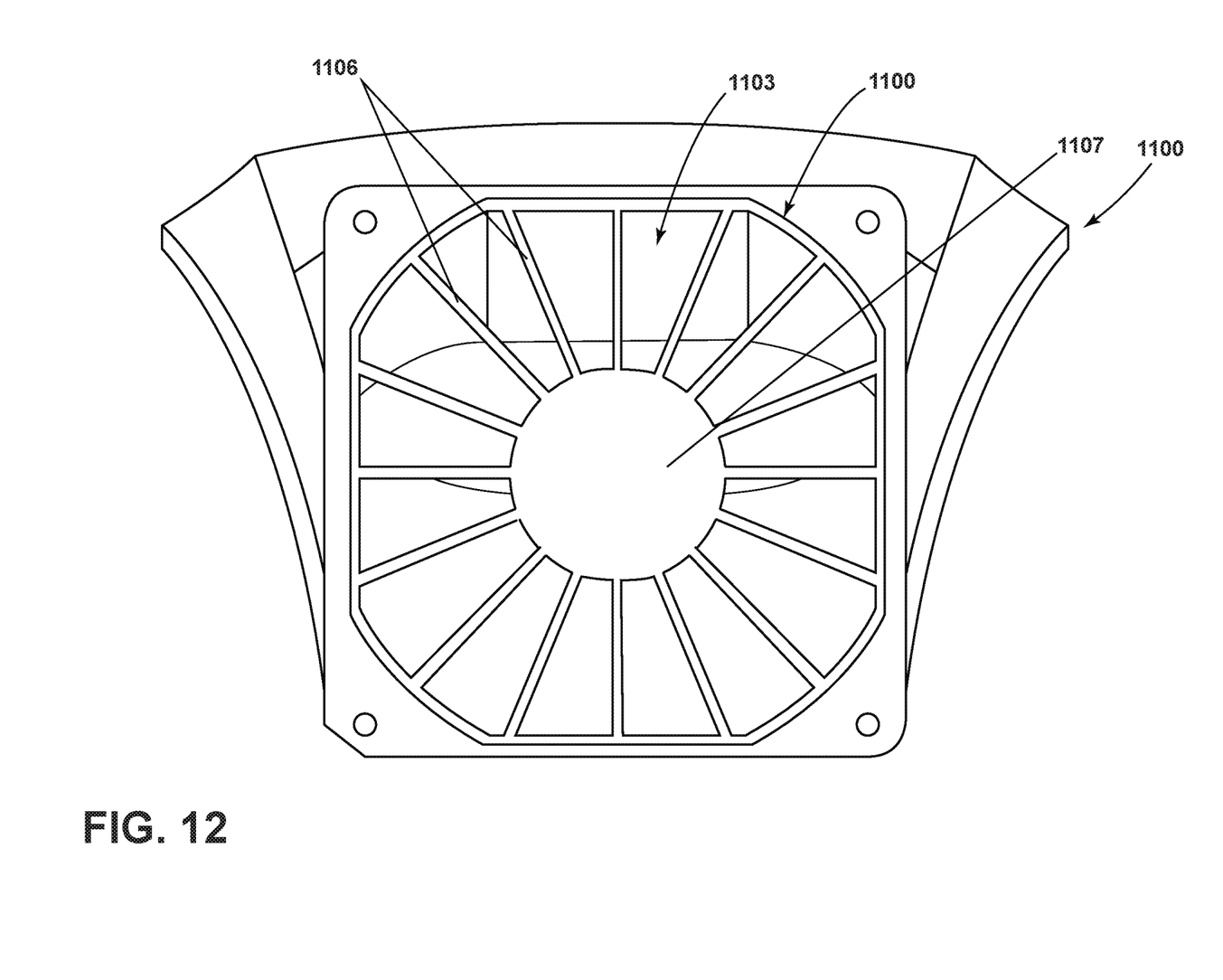
FIG. 12 shows a cross-sectional view of the duct taken along line XII-XII of FIG. 11, in accordance with various aspects described herein.

FIG. 12 illustrates a cross-sectional perspective view of the laminar flow device 1102 and duct 1103, taken along line XII-XII. As shown, the laminar flow blades 1106 can be circumferentially spaced about a hub 1107, and extend radially outward, terminating at the duct 1103. In another example configuration, the laminar flow blades 1106 can mirror the circumferential spacing of the fan blades (not shown).

Many other possible embodiments and configurations in addition to that shown in the above figures are contemplated by the present disclosure To the extent not already described, the different features and structures of the various embodiments can be used in combination with each other as desired. That one feature cannot be illustrated in all of the embodiments is not meant to be construed that it cannot be, but is done for brevity of description. Thus, the various features of the different embodiments can be mixed and matched as desired to form new embodiments, whether or not the new embodiments are expressly described. Combinations or permutations of features described herein are covered by this disclosure.

This written description uses examples to disclose embodiments of the invention, including the best mode, and also to enable any person skilled in the art to practice embodiments of the invention, including making and using any devices or systems and performing any incorporated methods. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ion generating device comprising:
   a housing having an opening;
   an anode and a cathode disposed within the housing and having a space between them;
   a power source having a negative terminal and a positive terminal with a first connection between the negative terminal and the anode and a second connection between the positive terminal and the cathode;
   a fluid conduit defining an interior and fluidly connected with the opening;
   an air mover disposed to direct an air flow through the space into the fluid conduit interior and out of the opening;
   at least one needle disposed relative to the fluid conduit such that the at least one needle is exposed to the interior of the fluid conduit, the at least one needle conductively connected with the anode; and
   a conductive surface disposed in the interior of the fluid conduit and conductively connected to the cathode, the conductive surface spaced from the at least one needle;
   wherein the conductive surface is an arc-shaped conductive surface and spaced from the at least one needle by a constant distance forming a radius of the arc.

2. The ion generating device of claim 1 wherein the at least one needle comprising tungsten.

3. The ion generating device of claim 1 wherein the tip diameter of the at least one needle is less than three micrometers.

4. The ion generating device of claim 1, further comprising at least two spaced needles.

5. The ion generating device of claim 4 wherein the at least two needles are spaced apart in a direction perpendicular to a direction of the directed air flow.

6. The ion generator device of claim 1 wherein the at least one needle is conductively connected with the anode by way of a resistor.

7. The ion generator device of claim 1 wherein the fluid conduit is a duct, and wherein at least a first portion of the needle is disposed in an exterior of the duct and a second portion of the needle is disposed in the interior of the duct.

8. The ion generator device of claim 7 wherein the needle includes a first end and a distal second end, wherein the second end includes the tip, and wherein the second portion of the needle includes the second end.

9. The ion generator device of claim 1 wherein the needle composition is selected based on at least a subset of considerations including: durability, corrosion resistance, ability to be sharpened, conductivity, sharpness, diameter, or needle geometry.

10. The ion generator device of claim 1 wherein the conductive surface is conductively connected to the cathode by way of a resistor selected to balance allowing a build up of charged ions to enable at least a partial repelling of ions during ion generator device operations while also least partially dissipating the build up of charged ions.

11. The ion generator device of claim 1, further comprising at least two needles spaced from the conductive surface, and wherein the arc-shaped conductive surface includes at least two arcs corresponding to the at least two needles, wherein each of the at least two arcs are spaced from a respective needle by a constant distance forming a radius of the arc.

12. The ion generator device of claim 11 wherein the arc-shaped conductive surface includes a crown shape.

13. The ion generator device of claim 11, wherein the conductive surface is shaped to balance allowing a build up of charged ions to enable at least a partial repelling of ions during ion generator device operations while also least partially dissipating the build up of charged ions.

14. The ion generator device of claim 11 wherein the constant distance is approximately 100 millimeters.

15. The ion generator device of claim 11 wherein the radius of the arc is approximately 50 millimeters.

16. The ion generator device of claim 1 wherein the at least one needle is disposed downstream of the conductive surface, relative to the direction of the air flow.

17. The ion generator device of claim 1 wherein the at least one needle is spaced from the conductive surface to prevent a dielectric breakdown of the air flow when the voltage potential between the at least one needle and the conductive surface is 10,000 Volts.

* * * * *